United States Patent [19]
Yamaguchi et al.

[11] Patent Number: 4,753,719
[45] Date of Patent: Jun. 28, 1988

[54] ION SENSOR AND METHOD OF MANUFACTURING SAME

[75] Inventors: Shuichiro Yamaguchi, Fuji; Takeshi Shimomura; Norihiko Ushizawa, both of Fujinomiya, all of Japan

[73] Assignee: Terumo Kabushiki Kaisha, Tokyo, Japan

[21] Appl. No.: 866,738

[22] Filed: May 27, 1986

[30] Foreign Application Priority Data

May 27, 1985 [JP] Japan .................................. 60-113667
Jun. 10, 1985 [JP] Japan .................................. 60-125665

[51] Int. Cl.$^4$ ............................................. G01N 27/30
[52] U.S. Cl. ..................................... 204/418; 204/416; 204/414; 204/400; 264/255; 264/262; 264/272.15; 264/275
[58] Field of Search ............... 204/400, 418, 414, 435, 204/415, 416, 419; 264/262, 255, 272.15, 275, 278

[56] References Cited

U.S. PATENT DOCUMENTS

| | | | |
|---|---|---|---|
| 3,926,764 | 12/1974 | Ruzicka et al. | 204/195 |
| 3,957,612 | 5/1976 | Niedrach et al. | 204/195 |
| 3,957,613 | 5/1976 | Macur | 204/195 |
| 4,052,285 | 10/1977 | Dobson | 204/418 |
| 4,214,968 | 7/1980 | Battaglia et al. | 204/195 |
| 4,549,951 | 10/1985 | Knudson et al. | 204/418 X |
| 4,563,263 | 1/1986 | Oyama et al. | 204/418 |

FOREIGN PATENT DOCUMENTS

| | | |
|---|---|---|
| 01186210 | 12/1985 | European Pat. Off. . |
| 3134760A | 2/1981 | Fed. Rep. of Germany . |
| 57-196116 | 7/1982 | Japan . |
| 59-57156 | 3/1984 | Japan . |
| 60-7357 | 1/1985 | Japan . |

OTHER PUBLICATIONS

Daniel Ammann, "Ion-Selective Microelectrodes", Principles, Design & Application, pp. 5-7, 66, 100.
Oyama et al, "Hydrogen Ion Selective Microelectrode Prepared by Modifying an Electrode with Polymers", Analytical Chemistry 1987, vol. 59, pp. 258-262, Jan. 1987.
Oyama, "Ion Selective Microelectrode Prepared by Modifying an Electrode with Polymers", International Electrical Symposium, Schaumburg, Ill., May 27-29 (1987).
Oyama et al, "A New Type of Ion-Selective Microelectrodes Using Electropolymerized Thin Films", j-4 Bioelectroanalytical Chemistry Symposium, Honolulu, Hawaii, Oct. 18-23, 1987.
Oyama et al, "Ion Selective Electrode Prepared by Modifying an Electrode with Polymers", Tokyo Seminar on Macromolecular Complexes, Tokyo Univ., Oct. 14-17, 1987.

*Primary Examiner*—John F. Niebling
*Assistant Examiner*—John S. Starsiak, Jr.
*Attorney, Agent, or Firm*—Burns, Doane, Swecker & Mathis

[57] ABSTRACT

Disclosed is an ion sensor having an ion-sensitive substrate provided within a tube at a position recessed from an open end of the tube and having an ion carrier membrane, which is selectively permeable to an ion of interest, filling the space between the opening of the tube and the surface of the ion-sensitive substrate on the open-end side of the tube. A method of manufacturing the ion sensor includes steps of inserting and retaining the ion-sensitive substrate in the tube, filling the space between the ion-sensitive substrate and the tube with a sol-like ion carrier membrane composition, and gelling the sol-like ion carrier membrane composition.

26 Claims, 10 Drawing Sheets

ION SENSOR AND METHOD OF MANUFACTURING SAME

BACKGROUND OF THE INVENTION (1) Field of the Invention

This invention relates to an ion sensor using an ion carrier membrane selectively permeable to an ion of interest.

(2) Description of the Prior Art

A known method of measuring a specific ion concentration in a liquid specimen uses a spectrum based on flame analysis. However, the method is disadvantageous in that it involves an apparatus of large size, cannot be applied for use at the site where the diagnosis is made and requires a long period of time to effect measurement.

An ion sensor known to be free of these disadvantages is a liquid-membrane electrode which uses a polymeric membrane that supports valinomycin, and which is provided with an internal liquid chamber. Owing to the provision of the internal liquid chamber, however, it is difficult to miniaturize the apparatus, and such problems as leakage and contamination are encountered.

To eliminate the drawbacks of the conventional ion sensor comprising the aformentioned liquid-membrane electrode, an ion sensor in which an ion-sensitive substrate is directly coated with an ion carrier membrane has been proposed. However, directly coating the ion-sensitive substrate with the ion carrier membrane uniformly to a desired thickness is not easy. For example, though a dip-coating method has been contemplated as the general means for obtaining the coating, it is difficult to adjust the viscosity of the dipping solution, the rate at which the substrate is lifted from the dipping solution, and the drying conditions. As a result, a variance tends to occur in membrane thickness. Another problem is that the process is troublesome and time consuming.

SUMMARY OF THE INVENTION

An object of the present invention is to provide an ion sensor which has a quick response, which is little affected by coexisting ions in a liquid specimen and by pulsation of the liquid, and which can be made very small in size.

According to the present invention, the foregoing object is attained by providing an ion sensor comprising a tube having at least one open end, an ion-sensitive substrate provided within the tube at a position recessed from the open end of the tube, and an ion carrier membrane selectively permeable to an ion of interest, the ion carrier membrane filling a space between the tube and the ion-sensitive substrate and being directly adhered to and coating a surface of the ion-sensitive substrate on the open-end side of the tube.

In embodiments of the invention, (1) the tube comprises an ion carrier membrane compositon.

(2) The tube comprises an insulator.

(3) The ion carrier membrane directly adhered to and coating the ion-sensitive substrate on the open-end side of the tube has a thickness of from 50 um to 3 mm.

(4) The ion carrier membrane comprises a base polymer containing an ion carrier and an electrolyte in dispersed form.

(5) The ion-sensitive substrate is selected from the group consisting of a linear body comprising platinum, silver, silver/silver chloride, copper, nickel or palladium, a carbon electrode having a surface coated with these substances, a carbon electrode having a surface coated with an oxidation-reduction membrane, a carbon electrode and a semiconductor ($SnO_2$, $In_2O_3$, SiC, etc.)

(6) The ion of interest is potassium ion, and the ion carrier is valinomycin.

(7) The ion of interest is sodium ion, and the ion carrier is benzo-15-crown-5.

(8) The peripheral surface of the ion-sensitive substrate showed to (3) and (5) is coated with an insulator.

Another object of the present invention is to provide a method of manufacturing an ion sensor, through which an ion-sensitive substrate (internal electrode) can be coated with an ion carrier membrane of any thickness simply and with good reproducibility.

A further object of the present invention is to provide a method of manufacturing an ion sensor which enables a user to work an ion carrier membrane into any desired thickness after the ion sensor has been manufactured.

According to the, present invention, the foregoing objects are attained by providing an ion sensor manufacturing method comprising the steps of inserting and retaining an ion-sensitive substrate in a tube having a predetermined inner diameter allowing insertion of the substrate, with the substrate occupying a position within the tube where a distal end of the substrate is recessed within the tube from a distal end thereof, filling a space between the ion-sensitive substrate and the tube, inclusive of a space between the distal end of the ion-sensitive substrate and the distal end of the tube, with a sol-like ion carrier membrane composition containing an ion carrier an electrolyte and a paste resin, and gelling the sol-like ion carrier membrane composition filling the abovementioned spaces.

Embodiments of the ion sensor manufacturing method of the present invention are as follows:

(1) The tube is selected from the group consisting of a ceramic, a hard plastic and a soft plastic.

(2) The ion carrier membrane composition further contains a plasticizer.

(3) The paste resin is non-expandable and exhibits little change with time.

(4) The ion carrier is selected from the group consisting of tetradodecylamine, valinomycin, crown ethers and a phosphate.

(5) The ion-sensitive substrate is selected from the group consisting of an oxidation-reduction membrane-coated carbon electrode, a silver/silver chloride electrode, a platinum electrode, a silver electrode, a copper electrode, a nickel electrode and a semiconductor electrode.

(6) The step of gelling the sol-like ion carrier membrane composition is carried out at a temperature of 80°–200° C.

(7) The distal end of the ion-sensitive substrate is recessed from the distal end of the tube by the thickness of a spacer in such a manner that the distal end of the ion-sensitive substrate comes to occupy a position recessed a prescribed distance from the distal end of the tube.

(8) The distal end of the tube is cut off so that the distal end of the ion-sensitive substrate comes to occupy a position recessed a prescribed distance from the distal end of the tube.

Further, according to the present invention, there is provided a method of manufacturing an ion sensor comprising the steps of inserting an ion-sensitive substrate into a tube having a predetermined inner diameter allowing insertion of the substrate, deciding the thickness of an ion carrier membrane by adjusting a positional relationship between a distal end of the substrate and a distal end of the tube, filling a space between the ion-sensitive substrate and the tube, inclusive of a space between the distal end of the ion-sensitive substrate and the distal end of the tube, with a sol-like ion carrier membrane composition containing an ion carrier, an electrolyte and a paste resin, and gelling the sol-like ion carrier membrane composition filling the above-mentioned spaces.

Embodiments of this ion sensor manufacturing method are as follows:

(1) The tube is selected from the group consisting of a ceramic, a hard plastic and a soft plastic.

(2) The ion carrier membrane composition further contains a plastic material.

(3) The paste resin is non-expandable and exhibits little change with time.

(4) The ion carrier is selected from the group consisting of tetradodecylamine, valinomycin, crown ethers and a phosphate.

(5) The ion-sensitive substrate is selected from the group consisting of an oxidation-reduction membrane-coated carbon electrode, a silver chloride electrode, a platinum electrode, a silver/silver electrode, a copper electrode, a nickel electrode and a semiconductor electrode.

(6) The step of gelling the sol-like ion carrier membrane composition is carried out at a temperature of 80°–200° C.

(7) The distal end of the ion-sensitive substrate is recessed from the distal end of the tube by the thickness of a spacer in such a manner that the distal end of the ion-sensitive substrate comes to occupy a position recessed a prescribed distance from the distal end of the tube.

(8) The distal end of the tube is cut off so that the distal end of the ion-sensitive substrate comes to occupy a position recessed a prescribed distance from the distal end of the tube.

Further, according to the present invention, there is provided a method of manufacturing an ion sensor comprising the steps of inserting and retaining an ion-sensitive substrate in a tube having a predetermined inner diameter allowing insertion of the substrate, with the substrate occupying a position within the tube where a distal end of the substrate is recessed within the tube from a distal end thereof, filling a space between the ion-sensitive substrate and the tube, inclusive of a space between the distal end of the ion-sensitive substrate and the distal end of the tube, with a sol-like ion carrier membrane composition containing an ion carrier, an electrolyte and a paste resin, gelling the sol-like ion.carrier membrane composition filling the abovementioned spaces, and deciding the thickness of the gelled ion carrier membrane at the distal end of the ion-sensitive membrane.

Embodiments of this ion sensor manufacturing method are as follows:

(1) The tube is selected from the group consisting of a ceramic, a hard plastic and a soft plastic.

(2) The ion carrier membrane composition further contains a plastic material.

(3) The paste resin is non-expandable and exhibits little change with time.

(4) The ion carrier is selected from the group consisting of tetradodecylamine, valinomycin, crown ethers and a phosphate.

(5) The ion-sensitive substrate is selected from the group consisting of an oxidation-reduction membrane-coated carbon electrode, a silver/silver chloride electrode, a platinum electrode, a silver electrode, a copper electrode, a nickel electrode and a semiconductor electrode.

(6) The step of gelling the sol-like ion carrier membrane composition is carried out at a temperature of 80°–200° C.

(7) The thickness of the gelled ion carrier membrane is decided by cutting off the distal end of the tube filled with the gelled ion carrier membrane in such a manner that the distal end of the tube has a prescribed distance from the distal end of the ion-sensitive substrate.

Other features and advantages of the present invention will be apparent from the following description taken in conjunction with the accompanying drawings, in which like reference characters designate the same or similar parts throughout the figures thereof.

DESCRIPTION OF THE PREFERRED EMBODIMENT

Figure 1:
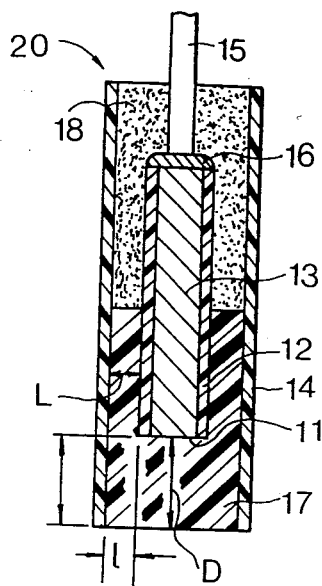
FIG. 1 is a partial sectional view of an ion sensor according to an embodiment of the present invention.
Figure 2:
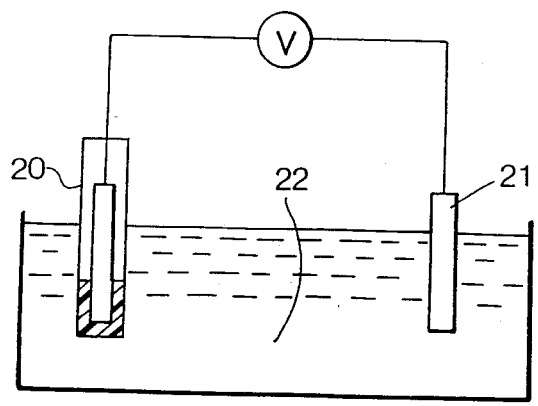
FIG. 2 is a schematic view showing an example in which the ion sensor of FIG. 1 is used.

To fabricate an ion sensor in accordance with the present invention, as shown in FIG. 1, the first step is to prepare an ion-sensitive substrate 13 comprising a platinum wire of 1 mm diameter the surface whereof, with the exception of a bottom surface (ion-sensitive portion) 11, is coated with an insulating paint 12. The ion-sensitive substrate 13 is retained within a tube (e.g. of Teflon) 14 having an inner diameter of 1.5 mm and a length of 50 mm. The substrate 13 is maintained at a prescribed positional relationship with respect to the tube 14 and has an upper edge to which a leading wire (e.g. a copper wire) 15 is fixedly secured via an electrically conductive adhesive or solder 16.

Next, while the positional relationship shown in FIG. 1 is maintained, a sol-like ion carrier composition 17 is injected into and fills the space between the lower portion of the tube 14 and the lower portion of the ion-sensitive substrate 13. The ion carrier composition is then gelled while being heated at a temperature of e.g. 80°–200° C. If necessary, this is followed by filling the space between the upper portion of the ion-sensitive substrate 13 and the upper portion of the tube 14 with an insulating adhesive 18, which is then allowed to harden. The finished product constitutes an ion sensor.

According to the present invention, a thickness D of the membrane on the bottom surface (sensitive surface) 11 of the ion-sensitive substrate 13 can be controlled to a constant value by adjusting as desired an offset distance d between the open end of the tube 14 and the bottom surface (sensitive surface) 11 of the ion-sensitive substrate 13. Further, a thickness L of the membrane extending horizontally from the side surface of the ion-sensitive substrate 13 can be controlled to a constant value by adjusting as desired a difference 1 between the inner diameter of the tube 14 and the outer diameter of the ion-sensitive substrate 13.

Depending upon the particular application, the tube 14 can be suitably selected from an inorganic material such as a ceramic, an organic material such as hard or soft plastic, an ion carrier membrane composition etc.

The ion carrier membrane composition comprises compositions chosen from several types of ion carriers and a paste resin in the form of a dispersion. The ion carrier composition may contain plastic or another additive so long as this does not detract from what is intented by the invention. Preferably, the paste resin is non-expandable and changes but little with time. The ion carrier can be suitably selected in dependence upon the type of ion to be measured. For instance, tetradodecylamine, valinomycin, crown ethers, a phosphate and the like can be used as the ion carrier.

No particular limitation is placed upon the ion-sensitive substrate 13, which can be selected from among an oxidation-reduction membrane-coated carbon electrode, a silver/silver chloride electrode, a platinum electrode, a silver electrode, a palladium electrode, a copper electrode, a nickel electrode and a semiconductor electrode.

The thickness D of the sensitive portion 17 of ion-sensitive substrate 13 generally is selected to be between 50 um and 3 mm.

Figure 3:
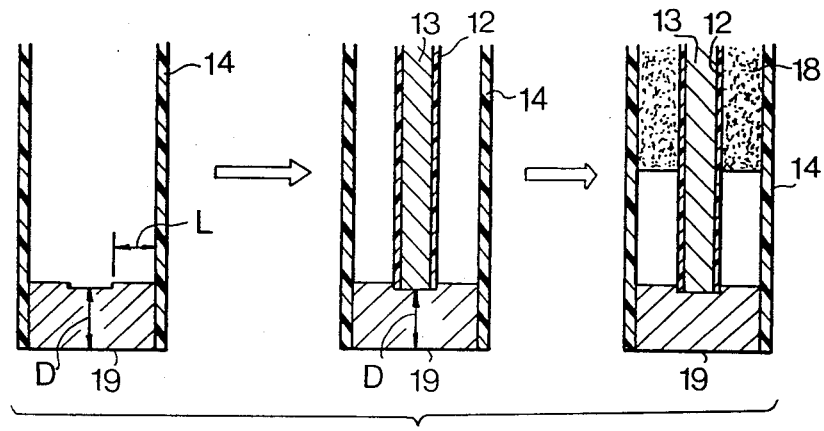
FIGS. 3(a)–(c) are views for describing a first embodiment of a method of manufacturing an ion sensor according to the present invention.
Figure 3:
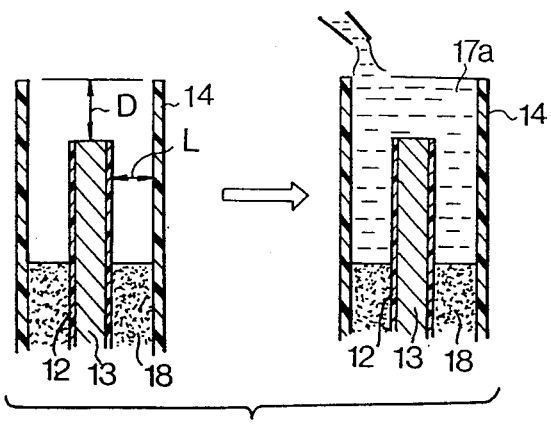
Figure 3:
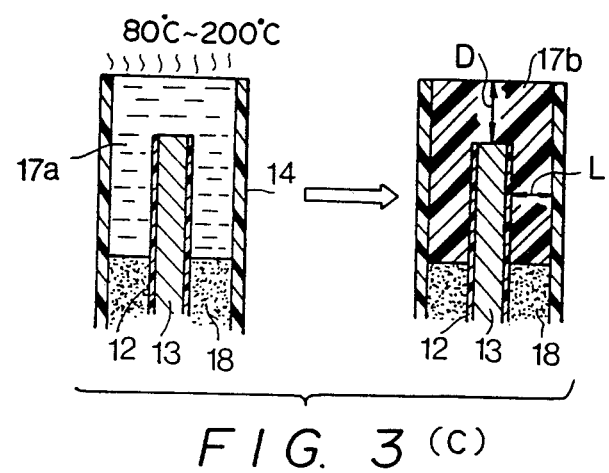
Figure 4:
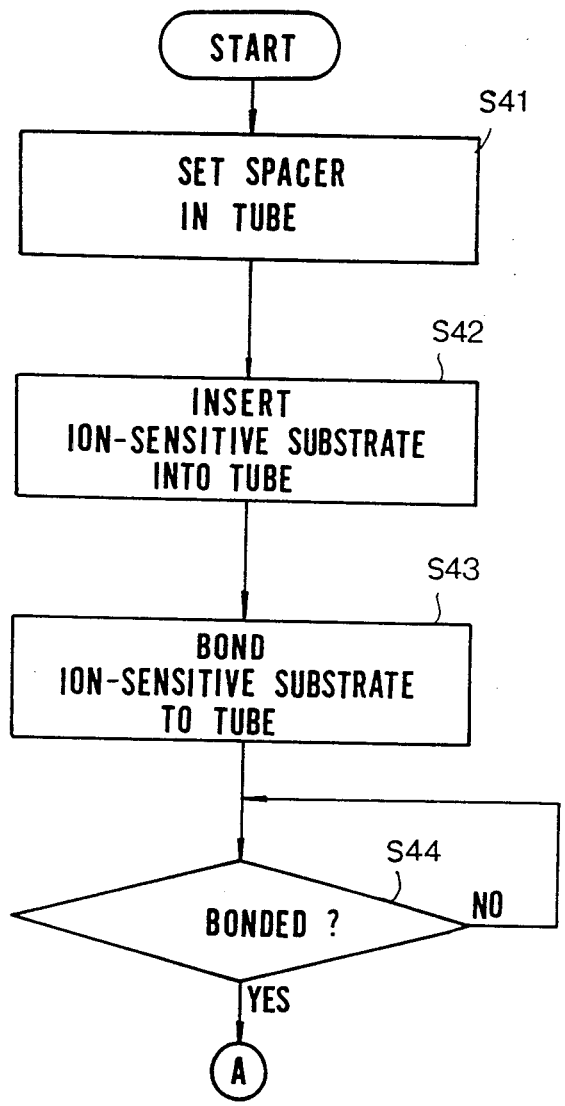
FIG. 4 (a), (b) are flowcharts illustrating the first embodiment of the method of manufacturing an ion sensor.
Figure 4:
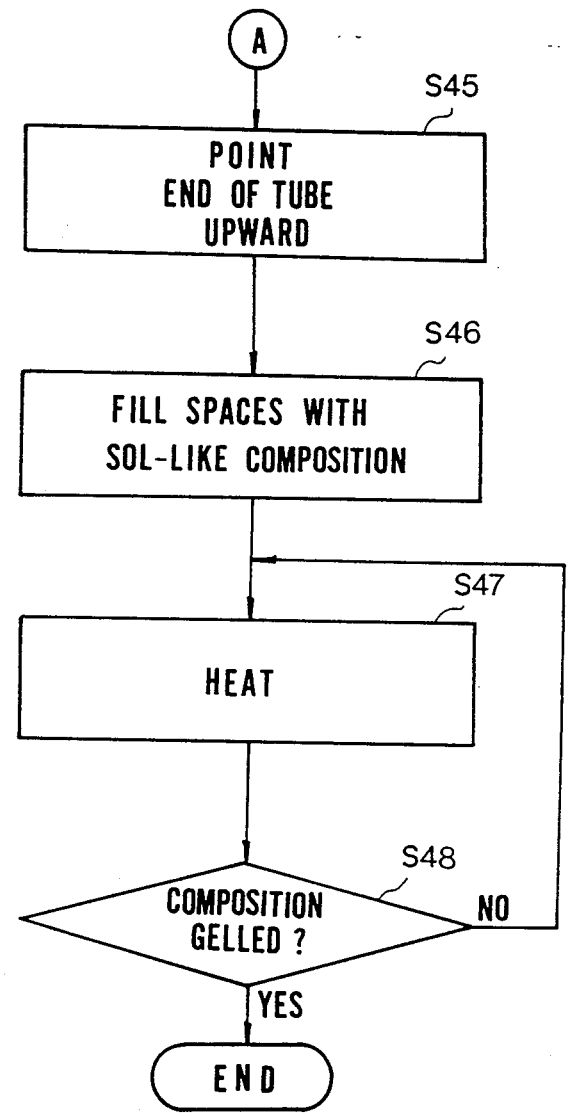
Figure 6:
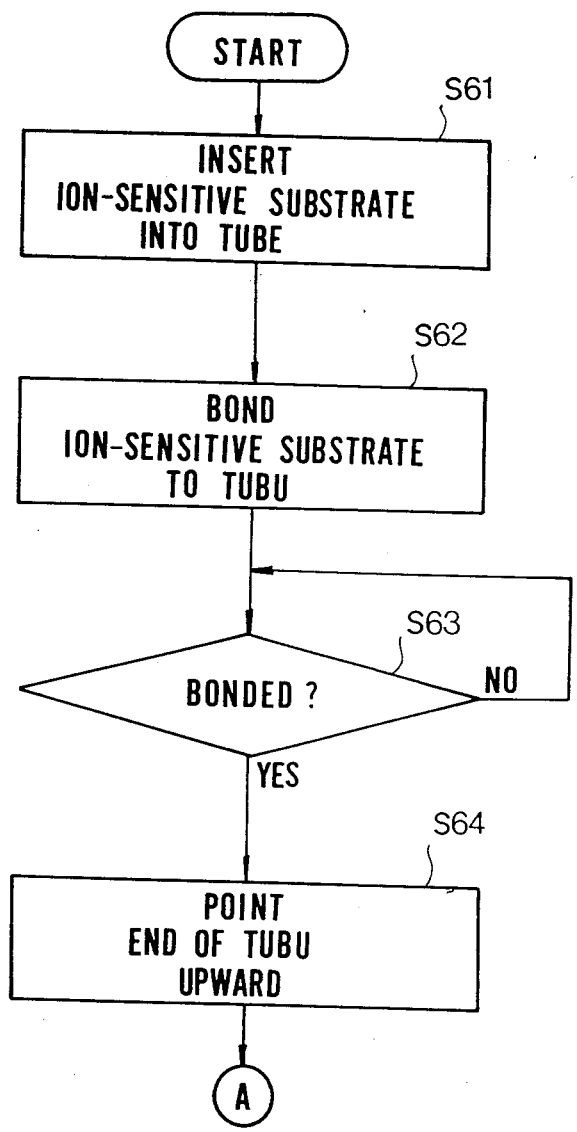
FIG. 6 (a), (b) are flowcharts illustrating the second embodiment of the method of manufacturing an ion sensor.
Figure 6B:
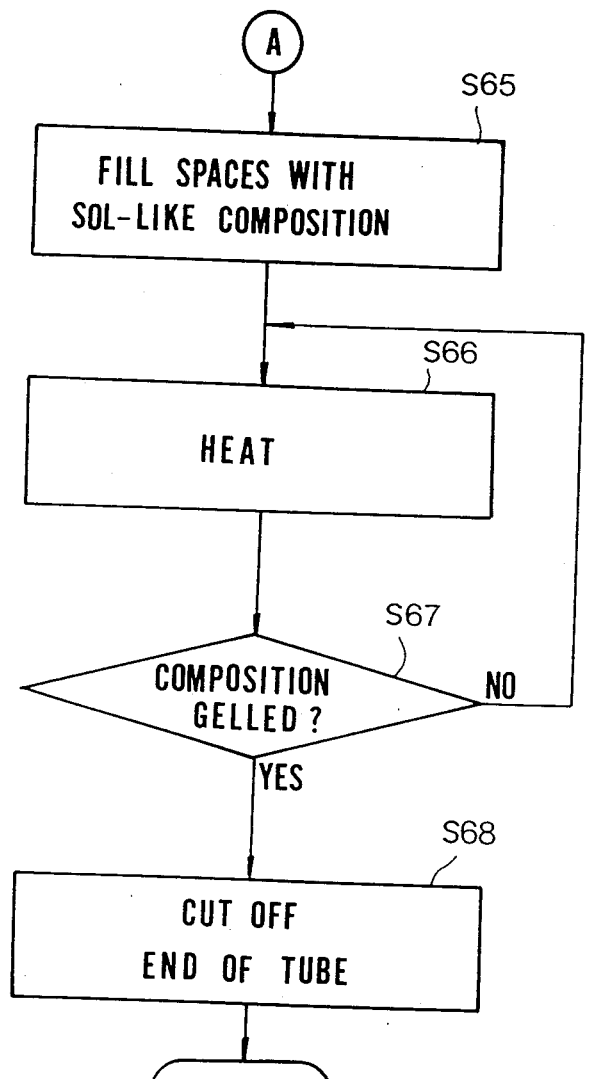

A first embodiment of a method of manufacturing the ion sensor is illustrated in FIGS. 3(a)-(c) and will now be described in detail with reference to the flowchart of FIG. 4 (a), (b).

First, at a step S41 of the flowchart, a spacer 19 having the thickness D of the membrane at the sensitive portion 17 is set in the tube 14, as shown at the extreme left of FIG. 3(a). The central portion of the spacer 19 is formed to have a recess capable of readily receiving the distal end of the ion-sensitive substrate 13. Next, at a step S42, the ion-sensitive substrate 13 is inserted into and set within the tube 14, as shown at the center of FIG. 3(a). This is followd by steps S43, S44, at which the ion-sensitive substrate is secured to the tube 14 by the insulating adhesive 18. Next, at a step S45, the distal end of the tube 14 is pointed upward, as shown on the left side in FIG. 3(b), after which the distal end portion of the tube 14 is filled with a sol-like ion carrier membrane composition 17a at a step S46, as shown on the right side of FIG. 3(b). This is followed by steps S47, S48, at which the sol-like ion carrier membrane composition 17a is converted into a gelled ion carrier membrane composition 17b by being heated at a temperature 80°-200° C., as shown in FIG. 3(c). This completes the manufacture of the ion sensors denoted by numeral 20.

Figure 5:
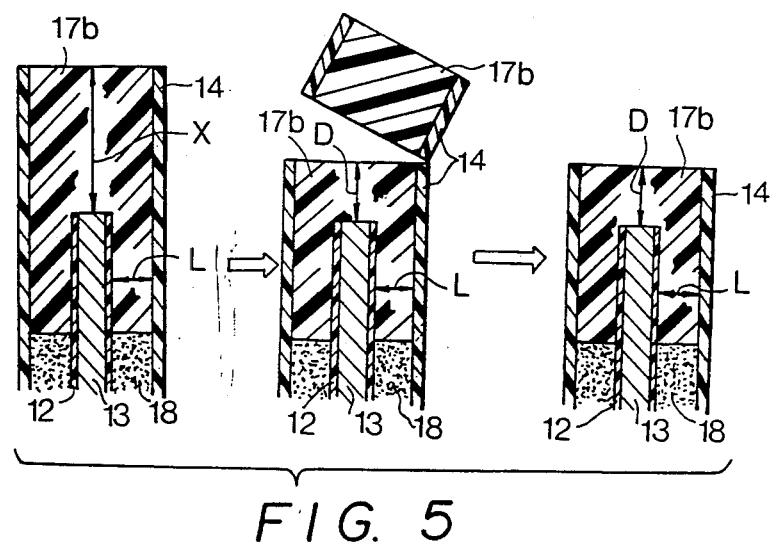
FIG. 5 is a view for describing a second embodiment of a method of manufacturing an ion sensor according to the present invention.

FIG. 5 is a view for describing a second embodiment of a method of manufacturing an ion sensor according to the present invention. In FIG. 5, steps similar to those shown in FIGS. 3(a)-(c) are not illustrated. This second embodiment of the manufacturing method will now be described in detail with reference to the flowchart of FIG. (a), (b).

First, at a step S61 of the flowchart, the ion-sensitive substrate 13 is inserted into the tube 14 and is recessed from the end of the tube 14 by a sufficient distance X. Next, at steps S62, S63, the ion-sensitive substrate 13 is secured to the tube 14 by the insulating adhesive 18. Then, at a step S64, the distal end of the tube 14 is pointed upward, after which it is filled with the sol-like ion carrier membrane composition 17a at a step S65. This is followed by steps S66, S67, at which the sol-like ion carrier membrane composition 17a is converted into a gelled ion carrier membrane composition 17b by being heated at a temperature 80°-200° C. Finally, at a step S68, the distal end of the tube 14 is cut off so that the membrane thickness of the sensitive portion 17 will be of a thickness D. This completes the manufacture of the ion sensor 20.

In the second embodiment of the manufacturing method described above, it is permissible to cut off the distal end of the tube 14 after the ion-sensitive substrate 13 is fixed to the tube 14 by the insulating adhesive 18 at the step S63. Further, the method of inserting and setting the ion-sensitive substrate 13 within the tube 14 is not limited to the illustrated embodiments.

In accordance with the method of manufacturing the ion sensor of the present invention, the technique used to coat the ion-sensitive substrate with the ion carrier membrane entails using the tube, inserting the ion-sensitive substrate into the tube, adjusting the positional relationship between them as desired, filling the space between them with the sol-type ion carrier membrane composition, and then gelling the composition. Accordingly, the coating step is simplified, treatment time is shortened and the thickness of the membrane can be readily controlled so that a carrier membrane of a constant thickness can be formed with excellent reproducibility. In addition, the method is particularly advantageous when manufacturing an ion sensor having an internal electrode of any shape. Furthermore, the ion carrier membrane thickness can be set by the user at his discretion.

Let us now describe several specific examples of an ion sensor in accordance with the present invention.

EXAMPLE 1

FIG. 1 illustrates an ion sensor according to an embodiment of the present invention. The ion-sensitive substrate 13 comprises the 1 mm-diameter platinum wire whose peripheral surface is coated with the insulating paint 12. The lower-end face 11 (ion-sensitive portion) of the ion-sensitive substrate 13 on the open side of the tube, and the peripheral surface of the lower portion of the ion-sensitive substrate 13, are directly coated with the ion carrier membrane 17 having thicknesses of 2-3 mm and 1 mm, respectively. Intimately affixed to the outer surface of the ion carrier membrane 17, with the exception of its lower surface, is the tube (e.g. of Teflon) 14 having an inner diameter of 1.5 mm and a length of 50 mm. The space between the upper portion of the ion-sensitive substrate 13 and the upper portion of the tube 14 is filled with the insulating adhesive (e.g. TB-2067 manufactured by Three Bond Corp.) 18. The leading wire (e.g. of copper) is connected to the upper end of the ion-sensitive substrate 13.

The following is used as the ion carrier membrane composition, assuming that the ion sensor is for measuring the concentration of potassium ion:

Potassium ion carrier composition

| | |
|---|---|
| Polyvinyl chloride paste resin (mean degree of polymerization: 1050) | 200 parts by weight |
| valinomycin | 10 parts by weight |
| Dioctylsebacate | 400 parts by weight |
| o-Nitrophenyloctyl ether | 400 parts by weight |

The valinomycin was dissolved in the o-nitrophenyloctyl ether, followed by the addition of the dioctylsebacate. Next, the polyvinyl chloride paste resin was added and the mixture was stirred sufficiently. Thereafter, the mixture was defoamed while being stirred for more than 5 hr less than a pressure $10^{-2}$ mmHg, thereby providing a plastisol-type ion carrier membrane composition. After the plastisol was packed into the electrode end portion 17, heating was effected immediately at a temperature of 140° C. using an oven, thereby enabling a gel to form in 2-5 min.

Next, by using the ion sensor 20, the electric potential between the ion sensor and a reference electrode (saturated sodium chloride calomel electrode) 21 was measured, thus providing a measurement of the potassium concentration in a liquid specimen 22. In order to determine the stability of the ion sensor according to the invention, measurement was continued for 10 hr in the specimen, which was a 50 ml KCl solution having a concentration of $10^{-4}$ M/l. As a result, there was obtained a constant potential difference ($300 \pm 5$ mV) (25.0° C.$\pm$0.1° C.).

Figure 8:
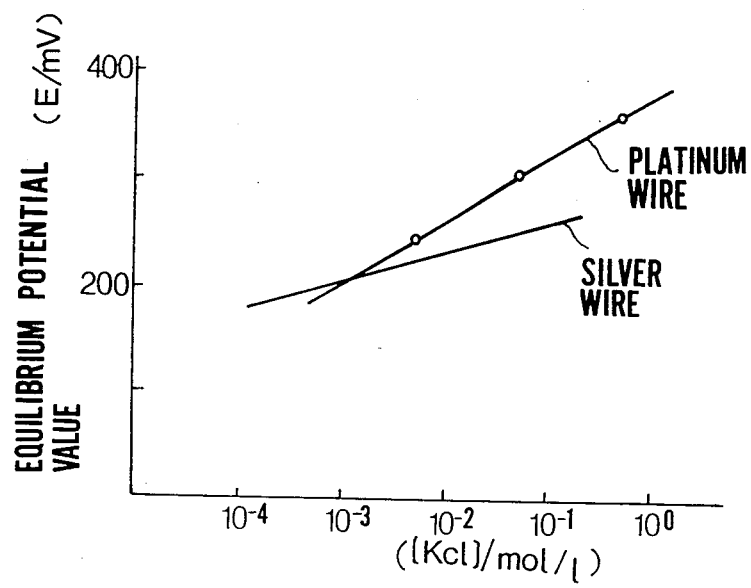

The potassium concentration in the liquid specimen was changed to $7.5 \times 10^{-3}$ M/l, $7.5 \times 10^{-2}$ M/l and $7.5 \times 10^{-1}$ M/l, and the equilibrium potential value was measured for each concentration. As shown in FIG. 8, the equilibrium potentials obtained where 245 mV, 305 mV and 360 mV, respectively, and a straight line (linear relationship) satisfying a Nernst equation was obtained from the correlation among these potential values. From the slope of the straight line, 58 mV/log ([K$^+$]/mol dm$^{-3}$) was obtained. The speed of response time was less than 60 sec.

EXAMPLE 2

Figure 7:
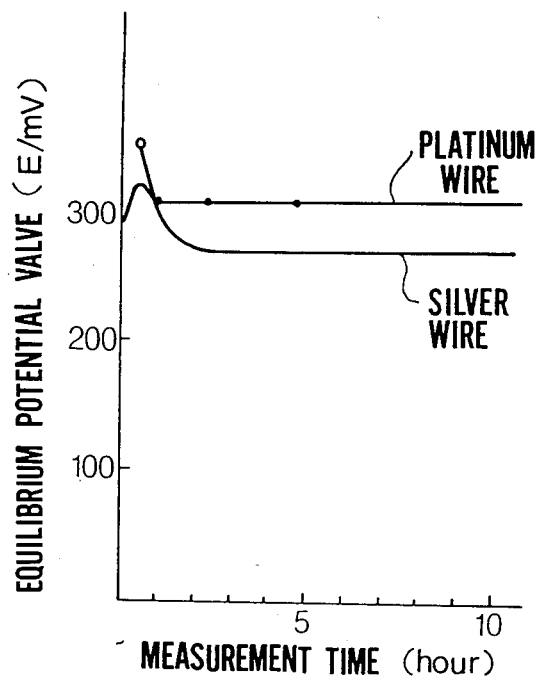
FIGS. 7 through 10 are diagrams illustrating results for a case where an electric potential is measured using the ion sensor of the illustrated embodiment.

An ion sensor was manufactured as in Example 1, the only difference being that a silver wire having a diameter of 1 mm was used in place of the platinum wire. The ion sensor with the silver wire was used to measure potassium ion concentration in the manner described above. The results are shown in FIGS. 7 and 8. The results shown in FIG. 7 are 10 hr hours of continuous measurement in a 50 ml KCl solution having a concentration of $1.5 \times 10^{-4}$ M/l. FIG. 8 shows the results obtained when the potassium ion concentration in the liquid specimen was changed to $2 \times 10^{-4}$ M/l $-9 \times 10^{-2}$ M/l. From the slope of the straight line shown in FIG. 8, 30 mV/log ([K$^+$]/mol dm$^{-3}$) was obtained.

EXAMPLE 3

Figure 9:
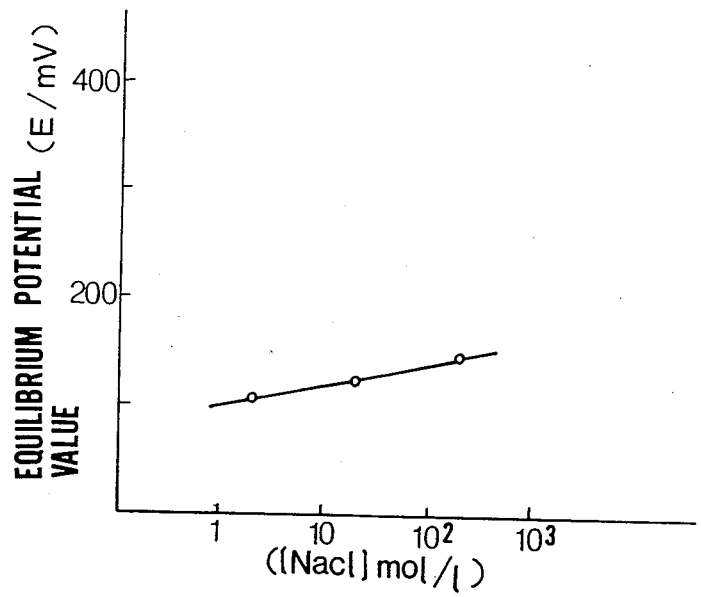

A sodium ion sensor using a silver wire having a diameter of 1 mm was manufactured as in Example 2, the only difference being that the wire was coated with a sodium ion carrier membrane, rather than a potassium ion carrier membrane, in which a paste-like polyvinyl chloride was used as a base polymer. The ion sensor was used to measure sodium ion concentration in a liquid specimen in the manner described above in connection with Example 2. The results are shown in FIG. 9. In this case, the sodium ion concentration in the liquid specimen was changed from 1 M/l $-10^3$ M/l. From the slope of the straight line shown in FIG. 9, 20 mV/decade [Na$^+$] (25° C.$\pm$0.1° C.) was obtained.

The sodium ion carrier membrane composition in this example was as follows:

Sodium ion carrier composition

| | |
|---|---|
| polyvinyl chloride paste resin (mean degree of polymerization: 1050) | 200 parts by weight |
| benzo-15-crown-5 | 10 parts by weight |
| dioctylsebacate | 400 parts by weight |
| nitrobenzene | 400 parts by weight |

EXAMPLE 4

Basal plane pyrolytic graphite (BPG) having a diameter of 1.3 mm was used in place of the platinum wire of Example 1. The following was used as the potassium ion carrier composition:

| | |
|---|---|
| bis [(benzo-15-crown-5)-4'-methyl] pimalate (Dojindo Laboratories) or bis (benzo-15-crown-5) | 10 " " 41 |
| dioctylsebacate | 200 " " " |
| polyvinyl chloride paste resin (mean degree of polymerization: 800) | 100 " " " |

This plastisol was gelled by being heated at a temperature of 140° C. for 5 min to form a polyvinyl chloride membrane having a thickness of 1 mm. One end of the BPG was bonded to the leading wire beforehand by using an electrically conductive adhesive (C-850-6 manufactured by Amicon K.K.).

Figure 10:
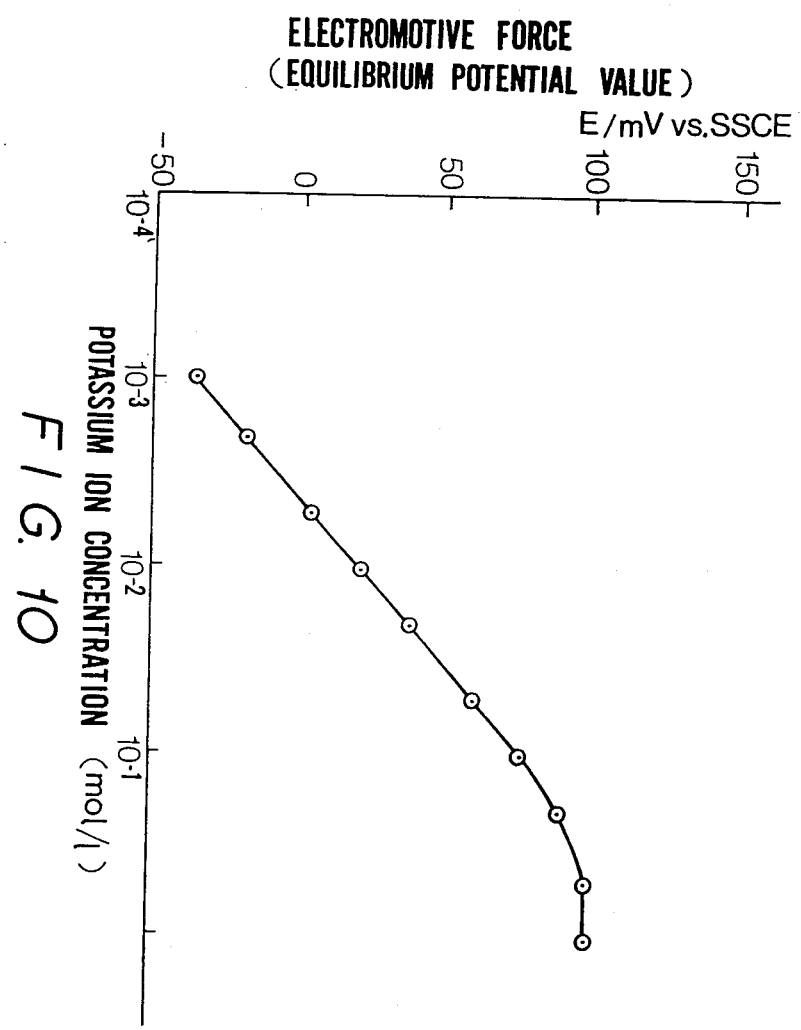

The electromotive force of the sensor thus formed was measured at a temperature of 37° C. while the potassium concentration in the liquid specimen was changed from $5 \times 10^{-4}$ to 1 mol/l. In the concentration range of from $1 \times 10^{-3}$ to $10^{-1}$ M, the electromotive force was linear, as illustrated in FIG. 10, with the slope of the straight line being 57 mV/log [K$^+$]. The time needed for a 95% response was less than 1 min in the range $10^{-3} - 10°$ M.

EXAMPLE 5

(sodium ion sensor)

As in Example 4, plastisol serving as a sodium ion carrier membrane was formed on the surface of the BPG electrode to a thickness of 1 mm under conditions the same as those used in Example 4. The sodium ion carrier membrane composition was as follows:

| | |
|---|---|
| bis [12-crown-4) methyl] methyldodecyl malonate (Dojindo Laboratories) | 10 parts by weight |
| dioctylsebacate | 200 parts by weight |
| polyvinyl chloride paste resin (mean degree of polymerization: 800) | 100 parts by weight |

The electromotive force of this electrode was measured at a temperature of 37° C. while the sodium ion concentration was changed using a 1 mM$-$1 M NaCl solution. As a result, good linearity was obtained between the electromotive force and the sodium ion concentration, and the slope of the straight line was 57 mV/log [Na+]/mol dm$^{-3}$. The time needed for 90% response was less than 1 min.

In the above embodiments, the ion carrier membrane thickness at the sensitive portion of the ion-sensitive substrate is from 2–3 mm. In general, however, the membrane thickness can be selected within the range from 50 um–3 mm. Further, the ion-sensitive substrate is not limited to that mentioned above but can be a member comprising silver/silver chloride or palladium, a carbon electrode whose surface is coated with these substances, a semiconductor ($SnO_2$, $In_2O_3$, SiC, etc.) or a carbon electrode.

The ions measured are not limited to potassium and sodium ion; concentrations of other ions can be measured by suitably selecting the ion carrier membrane.

Though the tube (designated at numeral 14 in FIG. 1) covering the ion carrier membrane is preferred in view of improving the durability and stability of the ion sensor, the tube can be deleted depending upon the circumstances.

Since the ion sensor of the present invention is adapted to measure an ion of interest via a comparatively thick ion carrier membrane selectively permeable to the particular ion, measurement is influenced neither by coexisting ions in the liquid specimen nor by pulsation of the liquid specimen. In addition, a quick response to the ion of interest is obtained. The apparatus can be made very small in size and improved in durability, and there is not danger of leakage since, unlike the prior art, the sensor does not require an internal chamber.

The ion sensor of the present invention can also be used upon being incorporated in various ion meters.

As many apparently widely different embodiments of the present invention can be made without departing from the spirit and scope thereof, it is to be understood that the invention is not limited to the specific embodiments thereof except as defined in the appended claims.

What we claim is:

1. An ion sensor comprising
a tube having an inner diameter of less than 3.0 mm and at least one open end,
an ion-sensitive substrate having two ends, said substrate, exclusive of the said two ends, being coated with an insulator and provided within said tube at a position recessed from the open end of the tube; and
an ion carrier membrane selectively sensitive to an ion of interest, said ion carrier membrane filling a space between said open end of said tube and a surface of said ion-sensitive substrate on said open-end side of said tube.

2. The ion sensor according to claim 1, wherein said tube comprises an ion carrier membrane composition.

3. The ion sensor according to claim 1, wherein said tube comprises an insulator selected from a group of materials consisting of ceramics, hard plastics and soft plastics.

4. The ion sensor according to claim 1, wherein said ion-sensitive substrate is selected from the group consisting of platinum, silver, silver/silver chloride, copper, nickel and palladium, a carbon electrode having a surface coated with these substances, a carbon electrode and a semiconductor.

5. An ion sensor manufacturing method comprising the steps of:

inserting and retaining an ion-sensitive substrate in a tube having a predetermined inner diameter allowing insertion of the ion-sensitive substrate, with said substrate occupying a position within the tube where a distal end of said substrate is recessed a prescribed distance from a distal end of the tube by the thickness of a spacer;

filling a space between the ion-sensitive substrate and the tube, inclusive of a space between the distal end of the ion-sensitive substrate and the distal end of the tube, with a sol-like ion carrier membrane composition containing an ion carrier and a paste resin; and gelling the sol-like ion carrier membrane composition filling said spaces.

6. The method according to claim 5, wherein the step of gelling the sol-like ion carrier membrane composition is carried out at a temperature of 80°–200° C.

7. A method of manufacturing an ion sensor comprising the steps of:

inserting and retaining an ion-sensitive substrate having two ends, wherein said substrate exclusive of the two ends is coated with an insulator, in a tube having a predetermined inner diameter allowing insertion of the ion-sensitive substrate, with said substrate occupying a position within the tube from a distal end thereof;

filling a space between the ion sensitive substrate and the tube, inclusive of a space between the distal end of the ion-sensitive substrate and the distal end of the tube, with a sol-like ion carrier membrane composition containing an ion carrier and a paste resin; and gelling the sol-like ion carrier membrane composition filling said spaces.

8. The method according to claim 7, wherein the step of gelling the sol-like ion carrier membrane composition is carried out at a temperature of 80°–200° C.

9. An ion sensor comprising:
a tube having at least one open end,
an ion-sensitive substrate provided within said tube at a position recessed from the open end of said tube; and
an ion carrier membrane comprising a polymer containing a paste resin of polyvinyl chloride group, benzo-15-crown, dioctylsebacate, and nitrobenzene,
said ion carrier membrane filling a space between said open end of said tube and a surface of said ion-sensitive substrate on said open-end side of said tube.

10. The ion sensor according to claim 9, wherein said substrate is provided with two ends, and further is coated with an insulator except at said two ends and said tube comprises an ion carrier membrane composition.

11. The ion sensor according to claim 9, wherein said tube comprises an insulator selected from a group of materials consisting of ceramics, hard plastics and soft plastics.

12. The ion sensor according to claim 9, wherein said ion-sensitive substrate is selected from the group consisting of platinum, silver, silver/silver chloride, copper, nickel and palladium, a carbon electrode having a surface coated with these substances, a carbon electrode and a semiconductor.

13. An ion sensor manufacturing method comprising the steps of:

inserting and retaining an ion-sensitive substrate in a tube having a predetermined inner diameter allowing insertion of the ion-sensitive substrate, with said substrate occupying a position within the tube where a distal end of said substrate is recessed within the tube from a distal end thereof;

filling a space between the ion-sensitive substrate and the tube, inclusive of a space between the distal end of the ion-sensitive substrate and the distal end of the tube, with a sol-like ion carrier membrane composition containing an ion carrier and a paste resin;

gelling the sol-like ion carrier membrane composition filling said spaces; and cutting off the distal end of the tube filled with the gelled ion carrier membrane in such a manner that the distal end of the tube is a prescribed distance from the distal end of the ion-sensitive substrate.

14. The method according to claim 13, wherein the step of gelling the sol-like ion carrier membrane composition is carried out at a temperature of 80°–200° C.

15. An ion sensor comprising:
a tube having at least one open end,
an ion-sensitive substrate provided within said tube at a position recessed from the open end of said tube; and
an ion carrier membrane comprising a polymer containing a paste resin of polyvinyl chloride group, bis(benzo-15-crown) and dioctylsebacate,
said ion carrier membrane filling a space between said open end of said tube and a surface of said ion-sensitive substrate on said open-end side of said tube.

16. The ion sensor according to claim 15, wherein said substrate is provided with two ends, and further is coated with an insulator except at said two ends and said tube comprises an ion carrier membrane composition.

17. The ion sensor according to claim 15, wherein said tube comprises an insulator selected from a group of materials consisting of ceramics, hard plastics and soft plastics.

18. The ion sensor according to claim 15, wherein said ion-sensitive substrate is selected from the group consisting of platinum, silver, silver/silver chloride, copper, nickel and palladium, a carbon electrode having a surface coated with these substances, a carbon electrode and a semiconductor.

19. An ion sensor comprising:
a tube having at least one open end,
an ion-sensitive substrate provided within said tube at a position recessed from the open end of said tube; and
an ion carrier membrane comprising a polymer containing a paste resin of polyvinyl chloride group, bis((12-crown-4) methyl)methyldodecyl malonate and dioctylsebacate,
said ion carrier membrane filling a space between said open end of said tube and a surface of said ion-sensitive substrate on said open-end side of said tube.

20. The ion sensor according to claim 19, wherein said substrate is provided with two ends, and further is coated with an insulator except at said two ends and said tube comprises an ion carrier membrane composition.

21. The ion sensor according to claim 19, wherein said tube comprises an insulator selected from a group of materials consisting of ceramics, hard plastics and soft plastics.

22. The ion sensor according to claim 19, wherein said ion-sensitive substrate is selected from the group consisting of platinum, silver, silver/silver chloride, copper, nickel and palladium, a carbon electrode having a surface coated with these substances, a carbon electrode and a semiconductor.

23. An ion sensor comprising:
a tube having at least one open end,
an ion-sensitive substrate provided within said tube at a position recessed from the open end of said tube; and
an ion carrier membrane comprising a polymer containing a paste resin of polyvinyl chloride group, valinomycin, dioctylsebacate, and o-nitrophenyloctyl ether,
said ion carrier membrane filling a space between said open end of said tube and a surface of said ion-sensitive substrate on said open-end side of said tube.

24. The ion sensor according to claim 23, wherein said substrate is provided with two ends, and further is coated with an insulator except at said two ends and said tube comprises an ion carrier membrane composition.

25. The ion sensor according to claim 23, wherein said tube comprises an insulator selected from a group of materials consisting of ceramics, hard plastics and soft plastics.

26. The ion sensor according to claim 23, wherein said ion-sensitive substrate is selected from the group consisting of platinum, silver, silver/silver chloride, copper, nickel and palladium, a carbon electrode having a surface coated with these substances, a carbon electrode and a semiconductor.

* * * * *